United States Patent
Yokota et al.

(10) Patent No.: US 8,636,705 B2
(45) Date of Patent: Jan. 28, 2014

(54) INJECTION NEEDLE ASSEMBLY AND MEDICINE INJECTION APPARATUS

(75) Inventors: Takayuki Yokota, Nakakoma-gun (JP);
Yoichiro Iwase, Ashigarakami-gun (JP);
Yoshinori Hishikawa, Nakakoma-gun (JP); Tsukasa Takahashi, Nakakoma-gun (JP)

(73) Assignee: Terumo Kabushiki Kaihsa, Shibuya-Ku, Tokyo (JP)

(*) Notice: Subject to any disclaimer, the term of this patent is extended or adjusted under 35 U.S.C. 154(b) by 408 days.

(21) Appl. No.: 12/894,689

(22) Filed: Sep. 30, 2010

(65) Prior Publication Data

US 2011/0077602 A1  Mar. 31, 2011

(30) Foreign Application Priority Data

Sep. 30, 2009  (JP) .................... 2009-228544
Sep. 30, 2009  (JP) .................... 2009-228545
Mar. 31, 2010  (JP) .................... 2010-082585

(51) Int. Cl.
*A61M 5/00* (2006.01)
*A61M 5/32* (2006.01)
*A61M 5/178* (2006.01)

(52) U.S. Cl.
USPC ........... 604/246; 604/240; 604/242; 604/272; 604/164.01; 604/167.03

(58) Field of Classification Search
USPC ......... 604/239, 117, 245, 246, 240, 187, 256, 604/533
See application file for complete search history.

(56) References Cited

U.S. PATENT DOCUMENTS

| | | | |
|---|---|---|---|
| 3,035,616 A | 5/1962 | Hamilton | |
| 5,964,737 A * | 10/1999 | Caizza | 604/239 |
| 7,544,189 B2 * | 6/2009 | Griffiths | 604/240 |
| 2007/0118077 A1 | 5/2007 | Clarke et al. | |
| 2010/0004626 A1 * | 1/2010 | Miller et al. | 604/506 |

FOREIGN PATENT DOCUMENTS

| | | |
|---|---|---|
| EP | 0 788 804 A2 | 8/1997 |
| JP | 61-28629 Y2 | 8/1986 |
| JP | 2001-299909 A | 10/2001 |
| JP | 2005-087521 A | 4/2005 |
| JP | 2006-116217 A | 5/2006 |
| JP | 2007-528281 A | 10/2007 |
| WO | 99/34850 A1 | 7/1999 |
| WO | WO 2005/087297 A1 | 9/2005 |
| WO | 2007/047403 A1 | 4/2007 |

OTHER PUBLICATIONS

Search Report dated Oct. 28, 2010, issued by the International Searching Authority in corresponding International patent application No. PCT/JP2010/066133.

* cited by examiner

*Primary Examiner* — Emily Schmidt
*Assistant Examiner* — Bradley G Thomas, Jr.
(74) *Attorney, Agent, or Firm* — Buchanan Ingersoll & Rooney PC

(57) ABSTRACT

An injection needle assembly includes a needle having a needle point to puncture skin, a needle hub including a first member which holds the needle, and a second member in which a discharge part of a syringe is to be fitted, and an elastic member disposed inside the second member to make liquid-tight close contact with the inner surface of the second member, with the elastic member having an insertion hole in which the needle tube is inserted.

20 Claims, 8 Drawing Sheets

INJECTION NEEDLE ASSEMBLY AND MEDICINE INJECTION APPARATUS

TECHNOLOGICAL FIELD

The present invention generally pertains to a medical device used to inject liquid medicine. More specifically, the invention concerns an injection needle assembly and a medicine injection apparatus configured to reduce the amount of liquid medicine left in the assembly or apparatus upon injection.

BACKGROUND DISCUSSION

The use of medicine injection apparatuses such as injectors typically involves sucking-in medicine from a vial. A vial is a medicine storage container in which medicine can be preserved for an extended time in a liquid or freeze-dried state. An opening part of the vial is normally sealed with a rubber stopper having a thickness of 3 to 5 mm. The rubber stopper is designed so that it does not permit leakage of the medicine therethrough, even when it is repeatedly pierced by a needle tube. Therefore, most of vaccines used often for group vaccination are sucked in from vials.

A common method of sucking medicine from a vial into a syringe involves first connecting a needle hub fitted with a suction needle tube of about 22 gauge to the syringe. Next, the suction needle tube is used to pierce the vial, and the liquid medicine is sucked into the syringe. Thereafter, the needle hub fitted with the suction needle tube is detached from the syringe, and a needle hub fitted with an injection needle tube is attached to the syringe. As a result, the medicine injection apparatus is in the state of being capable of injecting the medicine. After the medicine is injected (administered) by the medicine injection apparatus, some medicine is left in the needle tube, in the needle hub and in a distal portion of the syringe.

The skin is composed of three portions: the epidermis, the dermis, and the subcutaneous tissue. The epidermis is a layer of about 50 to 200 μm ranging from the surface of the skin, and the dermis is a layer of about 1.5 to 3.5 mm continuing from the epidermis. An influenza vaccine is ordinarily administered in a hypodermic or intramuscular manner, and, therefore, it is injected into a lower layer part of the skin or a part deeper than the lower layer part.

To reduce doses of the influenza vaccine, administration of the vaccine while taking as a target region a skin upper layer region where a lot of immunocytes are present has been investigated. The term "skin upper layer region" used here means the epidermis and the dermis, of the skin. The dose of the vaccine administered into the skin upper layer region is about 50 to 300 μL, preferably about 100 μL. Therefore, if the amount of the medicine left in the assembly or apparatus upon injection is large, the merit of reducing the quantity of antigen obtained by administering the vaccine into the skin upper layer region is lessened.

Further, the administration of a medicine into the skin upper layer region requires a higher injection pressure, as compared with hypodermic administration. Therefore, if the amount of air left in the engaging part between the syringe and the hub is increased, the remaining air forms a pressure interference zone, whereby it may be made impossible to secure an accurate dose.

Technologies for reducing the residual amount of medicine upon injection include a technology described in Japanese Utility Model Publication No. Sho 61-28629 (hereinafter referred to as Patent Document 1). A needle base part of the injection needle described in Patent Document 1 is provided with an insertion member and a stop member. The insertion member is formed from a synthetic rubber, a synthetic resin or the like which is elastic, and is so designed as to connect the injection needle with an injection cylinder and to fill up a dead volume of an injection needle attachment mouth (tip) formed at the distal end of the injection cylinder. The stop member is fitted in the tip of the injection cylinder.

Another technology for reducing the residual amount of medicine upon injection is described in Japanese Patent Laid-open No. 2006-116217 (hereinafter referred to as Patent Document 2). The injector described in Patent Document 2 has a configuration in which an injection needle and an outer cylinder having a cylinder tip in which to insert the injection needle are separable from each other. The cylinder tip of the outer cylinder has an opening part, the diameter of which is increased along the distal direction. In this case, the injection needle inserted into the cylinder tip is fitted in and put in contact with a minimum diameter part of the cylinder tip.

In the injection needle described in Patent Document 1, the operation of fitting the insertion member into the tip of the injection cylinder is troublesome. In the case of sucking a medicine from a vial, it is necessary to both attach the suction needle to the outer cylinder and attach the injection needle. Therefore, the injection needle described in Patent Document 1 is not well suited to use where a medicine is sucked from a vial so as to be used.

The injector described in Patent Document 2 is constructed such that the opening part formed at the cylinder tip of the outer cylinder is gradually enlarged in diameter along the distal direction, which permits the injection needle to be easily relatively inserted into the cylinder tip at the time of fitting the hub part to the outer cylinder. However, the injector described in Patent Document 2 makes it necessary to insert the needle tube into the cylinder tip of the outer cylinder by a predetermined length and fit the needle tube to a minimum diameter part of the cylinder tip. Thus, the base end (terminal end) of the needle tube must be precisely positioned in relation to the hub part fitted to the outer cylinder.

In the case of taper fitting between the injection cylinder and the injection needle, a dead volume would be generated between a distal end portion of the tip of the injection cylinder and the needle tube.

SUMMARY

According to one aspect, an injection needle assembly comprises a needle possessing a needle point to puncture skin of a living body, a needle hub including a first member which holds the needle tube and a second member in which a discharge part of a syringe is to be fitted, and an elastic member disposed inside the second member in liquid-tight close contact with an inner surface of the second member, the elastic member having an insertion hole in which the needle tube is positioned.

According to another aspect, a medicine injection apparatus includes a syringe having a discharge part, a needle tube having a needle point to be made to puncture a skin, a needle hub, and an elastic member. The needle hub has a first member which holds the needle tube and a second member in which the discharge part of the syringe is to be fitted. The elastic member is disposed inside the second member. The elastic member, which is disposed inside the second member to make liquid-tight close contact with an inner surface of the second member, has an insertion hole in which the needle tube is inserted.

Another aspect involves an injection needle assembly comprising: a needle, a first member, a second member, and an elastic member. The needle possesses a proximal end portion and a sharp distal end portion to puncture skin, and includes a through hole extending along a longitudinal extent of the needle and opening to the sharp distal end portion and to the proximal end portion of the needle. The first member possesses a through hole extending between proximal and distal ends of the first member, with the through hole of the first member being open at the proximal end of the first member and being open at the distal end of the first member. The needle is positioned in the through hole in the first member and is fixed in place in the through hole in the first member such that the sharp distal end of the needle projects distally beyond a distal end face of a distal end portion of the first member so the sharp distal end portion is exposed to puncture the skin and such that the proximal end of the needle projects proximally beyond a proximal end face of a proximal end portion of the first member so the proximal end of the needle is exposed. The second member possesses a through hole so the second member possesses an inner surface, with the through hole of the second member extending between proximal and distal ends of the second member, and the through hole in the second member being open at the proximal end of the second member and being open at the distal end of the second member. The proximal end portion of the through hole in the second member is configured to receive a discharge part of a syringe, and the proximal end portion of the first member is positioned inside the second member so that the outer peripheral surface of the proximal end portion of the first member faces the inner surface of the second member. The elastic member is disposed inside the second member and possesses an outer peripheral surface in liquid-tight contact with the inner surface of the second member. The elastic member also comprises an insertion hole extending throughout a longitudinal extent of the elastic member so that the elastic member possesses an inner surface, and a portion of the inner surface of the elastic member is in liquid-tight contact with an outer peripheral surface of the needle.

In the injection needle assembly and the medicine injection apparatus disclosed here, the needle tube is inserted through the elastic member disposed inside the second member, and the discharge part of the syringe is fitted into the second member. This helps ensure that communication between the discharge part of the syringe and the needle tube can be secured even if the base end (proximal end) of the needle tube is not precisely positioned relative to the needle hub. With the distance between the distal end of the discharge part of the syringe and the elastic member shortened or eliminated, the dead volume in the needle hub can be reduced, and the residual amount of a medicine upon injection can be decreased. The disclosed configuration makes it unnecessary to precisely adjust the position of the needle relative to the needle hub.

DETAILED DESCRIPTION

Figure 1:
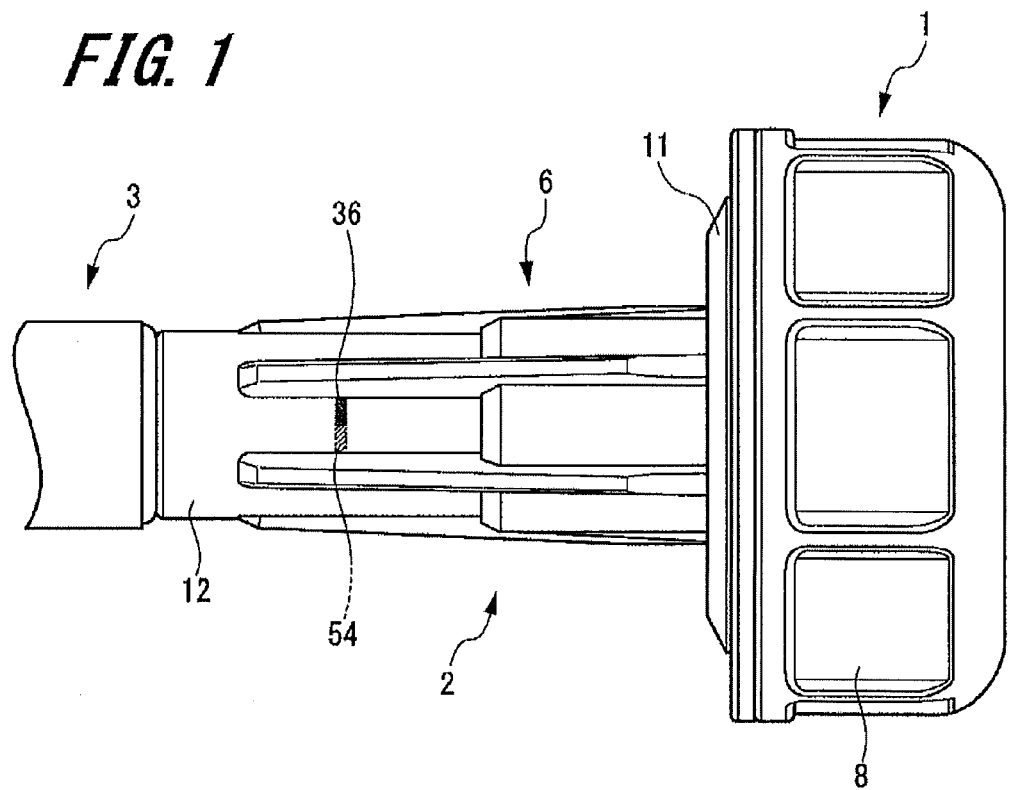
FIG. 1 is a side view of a first embodiment of a medicine injection apparatus disclosed here.

FIGS. 1-9 illustrate a number of embodiments of the injection needle assembly and the medicine injection apparatus disclosed here. In the drawings, common features and members are denoted by the same reference numeral. First embodiments of the medicine injection apparatus and the injection needle assembly are described below with reference to FIGS. 1 and 2.

[Medicine Injection Apparatus]

The medicine injection apparatus 1 disclosed here is used to puncture the surface of skin with a needle point and inject medicine into the upper layer part of the skin (skin upper layer region) following puncture of the skin. The medicine injection apparatus includes an injection needle assembly 2, and a syringe 3 to which the injection needle assembly 2 is connected in a disconnectable manner.

Figure 2:
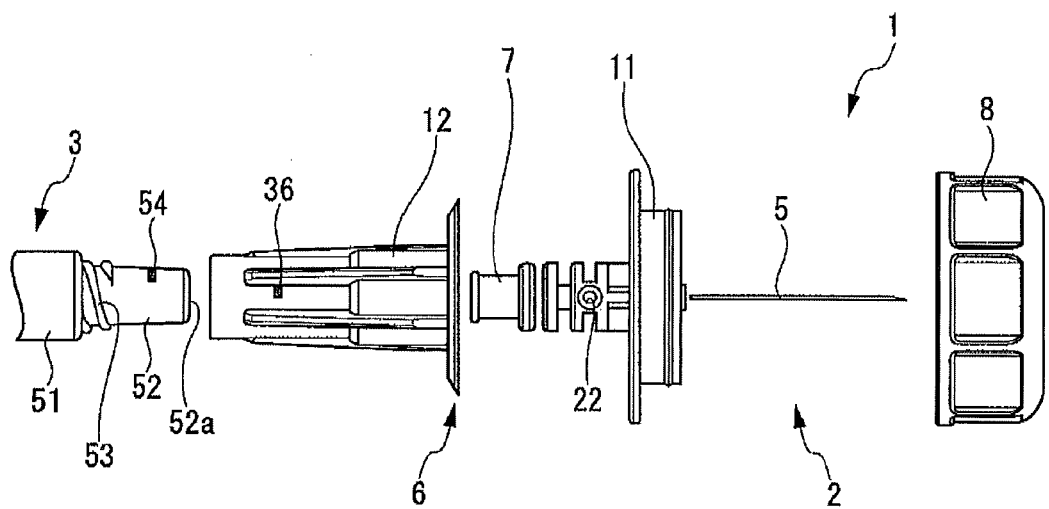
FIG. 2 is an exploded view of the first embodiment of the medicine injection apparatus.

As shown in FIG. 2, the injection needle assembly 2 includes a hollow needle tube 5 having a needle lumen or longitudinally extending through hole, a needle hub 6 to which the needle (needle tube) 5 is to be fixed, an elastic member 7 disposed inside the needle hub 6, and a cap 8 detachably attached to the needle hub 6. The needle hub 6 includes a first member 11 which holds the needle 5 and a second member 12 in which a discharge part 52 (to be described later) of the syringe 3 is to be fitted.

Additional details of the injection needle assembly 2 and the syringe 3 are described below, referring to FIGS. 3 and 4.

[Injection Needle Assembly]

A preferred needle 5 of the injection needle assembly 2 is a needle having a size (0.2 to 0.45 mm in outside diameter) conforming to 26 to 33 gauge according to ISO medical needle tube standard (ISO9626:1991/Amd. 1:2001(E)). More preferably, a needle tube 5 having a size of 30 to 33 gauge is used.

One end (the forward or distal end) of the needle 5 is provided with a sharp needle point 5A having a bevel (blade surface) 5a. Hereafter, the end of the needle 5 opposite the needle point 5A is referred to as the "proximal end 5B." The length of the bevel 5a along the axial direction of the needle tube 5 (the length is referred to as the "bevel length B") is preferably not more than 1.4 mm, which is the minimum thickness of the skin upper layer region to be described later (adults). In addition, the bevel length B is preferably not less than about 0.5 mm, which is a bevel length in the case where a 33 gauge needle tube is formed with a short bevel. In short, the bevel length B is preferably set in the range of 0.5 to 1.4 mm.

Further, it is preferable that the bevel length B is not more than 0.9 mm, which is the minimum thickness of the skin upper layer region (infants). It is more preferable that the bevel length B is in the range of 0.5 to 0.9 mm. The term "short bevel" means a bevel (blade surface) formed at an angle of 18 to 25° relative to the longitudinal direction of the needle, which bevel is commonly used for injection needles.

The material of the needle tube 5 may be, for example, stainless steel, but this is not limitative. Examples of other usable materials include such metals as aluminum, aluminum alloys, titanium, and titanium alloys. In addition, the needle tube 5 is not limited to a straight needle but may be a tapered needle which is tapered at least along a portion of its length. A tapered needle may be one in which the diameter of the proximal part of the needle is greater than the distal part, with an intermediate part having a tapered configuration. The cross-sectional shape of the needle tube 5 is not limited to a circle but may be a polygon such as a triangle.

Aspects of the needle hub 6 will now be described. The first member 11 and the second member 12 of the needle hub 6 are formed as separate members. The second member 12 is connected to the first member 11 while the first member 11 is in the state of holding the needle 5. Examples of material(s) for forming the first member 11 and the second member 12 include synthetic resins such as polycarbonate, polypropylene, polyethylene, etc.

The first member 11 includes a base part 15, an adjustment part 16, a stabilization part 17, and a guide part 18. The base part 15 possesses a cylindrical shape (inclusive of substantially cylindrical shape), and has end faces 15a and 15b perpendicular to the axial direction of the base part 15. The adjustment part 16 is provided at a central portion of the end face 15a of the base part 15, and is composed of a cylindrical projected part projecting in the axial direction of the base part 15. The axis of the adjustment part 16 coincides with the axis of the base part 15 (i.e., the adjustment part 16 and the base part 15 are coaxial).

The base part 15 and the adjustment part 16 each include a through-hole 21, extending along the axis of the base part 15 and the adjustment part 16, to be penetrated by the needle tube 5. The base part 15 includes an injection hole 22 (see FIGS. 2 and 4) for injecting an adhesive 20 (see FIG. 3) into the through-hole 21. The injection hole 22 opens to the outer peripheral surface of the base part 15, and communicates with the through-hole 21. By virtue of the adhesive 20 injected via the injection hole 22 into the through-hole 21, the needle tube 5 is secured to the base part 15.

Figure 3:
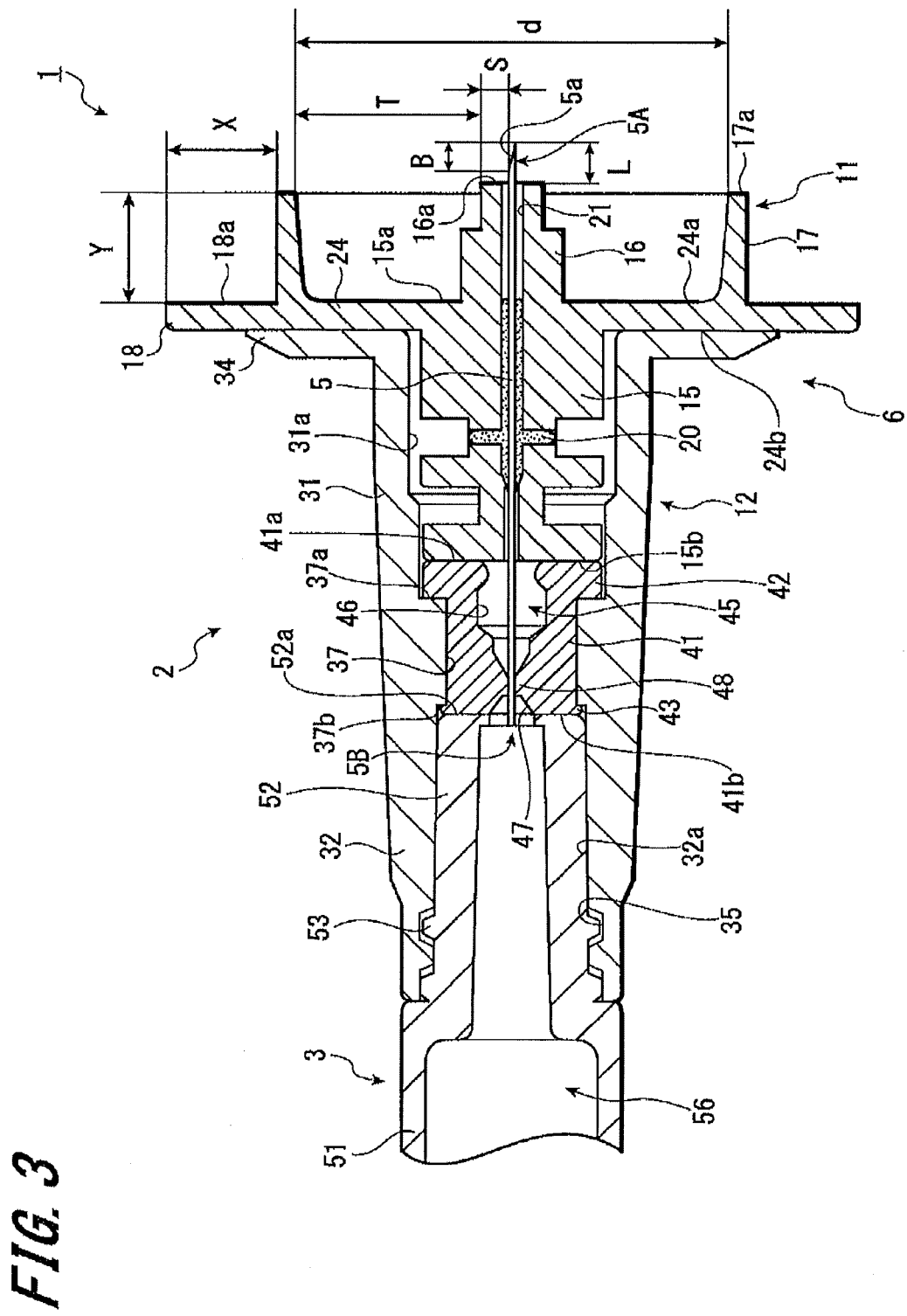
FIG. 3 is a cross-sectional view of the first embodiment of the medicine injection apparatus.
Figure 4:
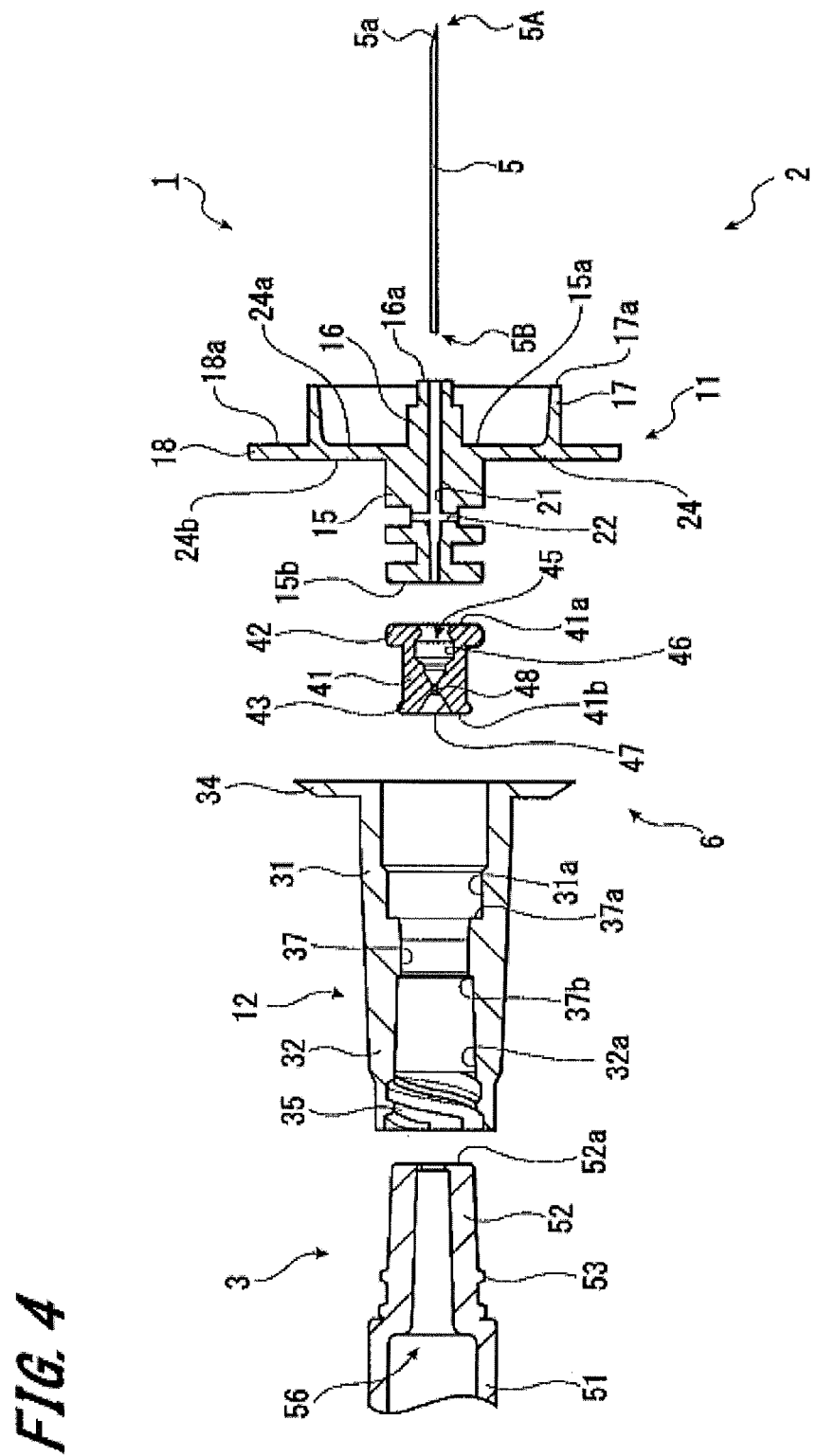
FIG. 4 is a cross-sectional view showing, in an exploded form, the first embodiment of the medicine injection apparatus.

The proximal end 5B side of the needle tube 5 protrudes proximally beyond the proximal end face 15b of the base part 15 as shown in FIG. 3. The base part 15 is inserted into the second member 12, its proximal end face 15b side first, and the proximal end 5B side of the needle tube 5 is inserted into and through an insertion hole 45 (described later) of the elastic member 7. The end face 15b of the base part 15 abuts the end face 41a (described later) of the elastic member 7.

The outer peripheral surface of the base part 15 includes a connection piece 24. The connection piece 24 is formed as a ring-shaped flange projecting in the radial directions of the base part 15, and has flat surfaces 24a and 24b which face opposite to each other in the axial direction of the base part 15. The second member 12 is connected to the flat surface 24b of the connection piece 24. In addition, tip portions (radially outer portions) of the connection piece 24 constitute a guide part 18. The guide part 18 will be described in detail later.

An end face of the adjustment part 16 constitutes a needle protrusion surface 16a from which the needle point 5A side of the needle 5 protrudes in the distal direction. Thus, as shown in FIG. 3, the needle 5 is fixed in place in the through hole 21 in the first member 11 such that the sharp distal end 5A of the needle 5 projects distally beyond the needle protrusion surface 16A (distal end face) of a distal end portion of the first member 11 so the sharp distal end portion 5A is exposed to puncture the skin. Also, the needle 5 is fixed in place such that the proximal end 5B of the needle 5 projects proximally beyond the proximal end face of a proximal end portion of the first member so the proximal end of the needle is exposed (i.e., uncovered).

The needle protrusion surface 16a is a flat surface orthogonal to the axial direction of the needle tube 5. When the needle tube 5 is positioned to puncture the skin upper layer region, the needle protrusion surface 16a contacts the surface of the skin to determine (control) the puncture depth. Specifically, the depth of puncture of the needle tube 5 into the skin upper layer region is determined by the length of that portion of the needle tube 5 which protrudes distally beyond needle protrusion surface 16a (this length will hereinafter be referred to as the "protrusion length L").

The thickness of the skin upper layer region corresponds to the depth ranging from the surface of the skin to the dermis layer, inclusive; in general, it is in the range of 0.5 to 3.0 mm. Therefore, the protrusion length L of the needle tube 5 is preferably set in the range of 0.5 to 3.0 mm.

Vaccines are generally administered into an arm region, and, in the case of administration into a skin upper layer region, the target site is preferably a thick-skinned shoulder peripheral region, particularly, a deltoid region. In view of this, the thickness of the skin upper layer region at the deltoid muscle was measured, for 19 infants and 31 adults. The measurement was conducted by imaging the skin upper layer region where ultrasonic reflectance is high, by use of an ultrasonic measuring instrument (NP60R-UBM, a high-resolution echo system for small animals, produced by NEPA GENE CO., LTD.). The measurements were in log normal distribution and, therefore, the range of MEAN±2SD was determined by use of geometric mean.

As a result, the thickness of the skin upper layer region at the deltoid muscles of infants was found to be 0.9 to 1.6 mm. The thickness of the skin upper layer region at the deltoid muscles of adults was found to be 1.4 to 2.6 mm in a distal region, 1.4 to 2.5 mm in a central region, and 1.5 to 2.5 mm in a proximal region. From these measurements, it was confirmed that the thickness of the skin upper layer region at the deltoid muscle is not less than 0.9 mm in infants, and not less than 1.4 mm in adults. Accordingly, it is preferable that the protrusion length L of the needle tube 5, in injection into the skin upper layer region at the deltoid muscle, is in the range of 0.9 to 1.4 mm.

With the protrusion length L set in this manner, the bevel 5a of the needle point 5A can be securely positioned in the skin upper layer region. This results in the needle hole (liquid medicine discharge port) opening at the bevel 5a being located in the skin upper layer region, irrespective of the position in the bevel 5a the needle hole is located. Even when the liquid medicine discharge port is located in the skin upper layer region, the liquid medicine will flow into the subcutaneous region if the needle point 5A pierces to a position deeper than the skin upper layer region. Therefore, it is important that the bevel 5a is securely located within the skin upper layer region.

In the case of a needle tube thicker (greater in diameter) than 26 gauge, it is difficult to set the bevel length B to be not more than 1.0 mm. In order to set the protrusion length L of the needle tube 5 to within the preferable range (0.9 to 1.4 mm), therefore, it is preferable to use a needle tube thinner (smaller in diameter) than 26 gauge.

The needle protrusion surface 16a is so formed that the distance S from its peripheral edge to the outer peripheral surface of the needle tube 5 is not more than 1.4 mm, preferably in the range of 0.3 to 1.4 mm. This distance S between the outer peripheral edge of the needle protrusion surface 16a and the outer peripheral surface of the needle 5 is determined by taking into account that a pressure is exerted on a wheal or blister formed by injection of the medicine into the skin upper layer region. Specifically, the needle protrusion surface 16a is set to be sufficiently smaller than the wheal/blister to be formed in the skin upper layer region and, hence, does not inhibit the formation of the blister. This helps ensure that even when the needle protrusion surface 16a presses against the skin in the surroundings of the needle tube 5, the medicine being injected can be prevented from leaking.

The stabilization part 17 is cylindrically shaped and protrudes from the flat surface 24a of the connection piece 24 provided on the base part 15. The needle tube 5 and the adjustment part 16 are disposed in a cylinder hole of the stabilization part 17 (the cylindrical interior surrounded by the cylindrical stabilization part 17). In other words, the stabilization part 17 is formed in a cylindrical shape and surrounds the adjustment part 16 penetrated by the needle 5, and is radially outwardly spaced from the needle point 5A of the needle tube 5.

The cap 8 is detachably attached to the stabilization part 17. The cap 8 covers the needle point 5A of the needle tube 5. This helps ensure that at the time of mounting the needle hub 6 to the syringe 3, the needle point 5A is inhibited or prevented from touching a user's finger or the like. This also helps ensure that the medicine injection apparatus 1 or the injection needle assembly 2 after use can be constantly maintained in a safe condition. Accordingly, the user can carry out an operation of discarding the used medicine injection apparatus 1 or injection needle assembly 2 or the like operation without anxiety.

As shown in FIG. 3, the distal end face 17a of the stabilization part 17 is located on the side of the proximal end 5B of the needle tube 5 relative to the needle protrusion surface 16a of the adjustment part 16. That is, the distal end face 17a of the stabilization part 17 is positioned proximally of the protrusion surface 16a of the adjustment part 16. When the needle point 5A of the needle tube 5 punctures a living body, the needle protrusion surface 16a first comes into contact with the surface of the skin, and thereafter the surface of the skin touches the end face 17a of the stabilization part 17. In this instance, the contact of the end face 17a of the stabilization part 17 with the skin helps stabilize the medicine injection apparatus 1, whereby the needle tube 5 can be kept in a posture of being substantially perpendicular to the skin.

When the end face 17a of the stabilization part 17 is located on the same plane as the needle protrusion surface 16a, or more preferably is located on the side of the needle point 5A of the needle tube 5 (i.e., distally) relative to the needle protrusion surface 16a, the needle 5 can be maintained in a posture of being substantially perpendicular to the skin. Taking into account the bulging of the skin when the stabilization part 17 is pressed against the skin, the distance between the end face 17a of the stabilization part 17 and the needle protrusion surface 16a along the axial direction is preferably set to be not more than 1.3 mm.

In addition, the inside diameter d of the stabilization part 17 is equal to or greater than the diameter of the wheal or blister to be formed in the skin. Specifically, the inside diameter d of the stabilization part 17 is so set that the distance T from the inner wall surface of the stabilization part 17 to the outer peripheral edge of the needle protrusion surface 16a is in the range of 4 to 15 mm. This helps ensure that hindrance of wheal/blister formation due to exertion of a pressure on the wheal/blister from the inner wall surface of the stabilization part 17 can be avoided or obviated.

It suffices that the distance T from the inner wall surface of the stabilization part 17 to the peripheral edge of the needle protrusion surface 16a is not less than 4 mm, and there is no upper limit for the distance T. However, an increase in the distance T causes an increase in the outside diameter of the stabilization part 17, which makes it difficult to bring the whole part of the end face 17a of the stabilization part 17 into contact with the skin in the case where the needle tube 5 is used to puncture a slender arm, such as the arm of an infant. Taking the slenderness of an infant's arm into account, therefore, it is preferable that the distance T is 15 mm at maximum.

When the distance S from the peripheral edge of the needle protrusion surface 16a to the outer peripheral surface of the needle 5 is not less than 0.3 mm, the adjustment part 16 will not enter into the skin. Taking into account the distance T (not less than 4 mm) from the inner wall surface of the stabilization part 17 to the peripheral edge of the needle protrusion surface 16a and the diameter (about 0.3 mm) of the needle protrusion surface 16a, therefore, the inside diameter d of the stabilization part 17 is preferably not less than 9 mm.

The shape of the stabilization part 17 is not limited to a cylindrical shape; for example, the shape may be a cylinder (tube) with a polygonal sectional shape, such as a tetragonal prism, a hexagonal prism or the like having a cylinder (tube) hole in the center thereof.

The guide part 18 is that portion of the connection piece 24 which is located on the tip side (radially outer peripheral side) relative to the stabilization part 17. The guide part 18 has a contact surface 18a to be brought into contact with skin. The contact surface 18a is a part of the flat surface 24a of the connection piece 24, and is a flat surface substantially parallel to the end face 17a of the stabilization part 17. By pressing the stabilization part 17 against skin until the contact surface 18a of the guide part 18 makes contact with the skin, a force with which the stabilization part 17 and the needle tube 5 are pressed against the skin can always be secured to be not less than a predetermined value. This helps ensure that the portion of the needle tube 5 which protrudes from the needle protrusion surface 16a (the portion corresponding to the protrusion length L) securely punctures the skin.

The distance (hereinafter referred to as "guide part height") Y from the contact surface 18a of the guide part 18 to the distal end face 17a of the stabilization part 17 is so set that the needle tube 5 and the stabilization part 17 can be pressed against skin with an appropriate pressure, resulting in appropriate puncture. This helps ensure that the pressure exerted on the skin by the needle tube 5 and the stabilization part 17 is guided by the guide part 18, the needle point 5A (the bevel 5a) of the needle tube 5 can be securely located in the skin upper layer region, and the user can get a feeling of security. The appropriate pressure with which the needle tube 5 and the stabilization part 17 are pressed against the skin is, for example, 3 to 20 N.

Where the inside diameter d of the stabilization part 17 is in the range of 11 to 14 mm, the guide part height Y is appropriately determined based on the length (hereinafter referred to as "guide part length") X from the tip surface (radially outside surface) of the guide part 18 to the outer peripheral surface of the stabilization part 17. For example, where the inside diameter d of the stabilization part 17 is 12 mm and the guide part length X is 3.0 mm, the guide part height Y is set in the range of 2.3 to 6.6 mm.

Aspects and details of the second member 12 are now described below. The second member 12 is a cylindrical (inclusive of substantially cylindrical) tubular shape. One end portion in the axial direction of the second member 12 (distal end portion) is an insertion part 31 in which the base part (proximal part) 15 of the first member 11 is to be inserted, and the other end portion (proximal end portion) is a fitting part 32 in which the discharge part 52 of the syringe 3 is to be fitted. A cylinder (tube) hole 31a of the insertion part 31 is sized correspondingly to the base part 15 of the first member 11.

The insertion part 31 includes a fixation piece 34 to be connected to the connection piece 24 of the first member 11. The fixation piece 34 is formed as a ring-shaped flange projecting radially outward continuously from the distal end of the insertion part 31. The flat surface 24b of the connection piece 24 provided on the first member 11 abuts on and is firmly attached to the fixation piece 34. Examples of the method for firmly attaching the fixation piece 34 and the connection piece 24 to each other include adhesion with an adhesive, ultrasonic fusing, laser fusing, fixation with a set screw(s), etc.

The cylindrical (tubular) hole 32a of the fitting part 32 is sized correspondingly to the discharge part 52 of the syringe 3, and the inner diameter of the hole 32a continuously decreases toward the side of the insertion part 31. An inner surface of the fitting part 32 is formed with a screw groove 35 for screw engagement with the discharge part 52 of the syringe 3.

In addition, as shown in FIG. 1, the outer peripheral surface of the fitting part 32 is provided with a hub-side indication part 36 as a recognition part for permitting the user to recognize that the fitting of the discharge part 52 is completed. When the discharge part 52 is fitted into the fitting part 32, the hub-side indication part 36 coincides with a syringe-side indication part 54 (described later) provided on the discharge part 52, in the circumferential direction of the second member 12. This permits the user to recognize that the fitting of the discharge part 52 into the fitting part 32 is completed. In this embodiment, therefore, at least the second member 12 of the needle hub 6 is formed from a transparent or semi-transparent synthetic resin so that the syringe-side indication part 54 can be visually observed or checked through the fitting part 32.

The recognition part described above may be composed of a structure in which one of a screw part 53 and the screw groove 35 is provided with a projection at its proximal portion and the other is provided at its proximal portion with a recess for engagement with the projected part. In this case, engagement between the projection and the recess permits the user to recognize that the fitting of the discharge part 52 into the fitting part 32 is completed.

Between the insertion part 31 and the fitting part 32 is provided an engagement part 37 for engagement with the elastic member 7. The engagement part 37 is formed as a stepped part projecting radially inward from an inner surface of the second member 12, and has engaging surfaces 37a and 37b substantially orthogonal to the axial direction of the second member 12. The engaging surface 37a of the engagement part 37 is engaged with a flange part 42 (described later) of the elastic member 7, and the engaging surface 37b is engaged with a stopper projection 43 of the elastic member 7. Details and aspects of the elastic member 7 are now described.

The elastic member 7 is disposed inside the second member 12 of the needle hub 6, and is interposed between the first member 11 and the syringe 3. The elastic member 7 thus arranged fills-up, in a liquid-tight manner, a gap between the proximal end face of the first member 11 and the distal end face of the second member 12. The elastic member 7 includes a body part 41, a flange part 42 at one end in the axial direction of the body part 41, and the stopper projection 43 at the other end of the body part 41.

The body part 41 is cylindrically shaped (inclusive of substantially cylindrically-shaped), and has end faces 41a and 41b perpendicular to the axial direction of the body part 41. The proximal end face 15b of the base part 15 of the first member 11 abuts one end face (distal end face) 41a of the body part 41, and the distal end face of the discharge part 52 provided as part of the syringe 3 abuts the other end face (proximal end face) 41b of the body part 41. In other words, the other end face 41b constitutes an abutting face on which the distal end of the discharge part 52 is to abut.

The body part 41 is provided with an insertion hole 45 in and through which the proximal end 5B side of the needle tube 5 protruding from the proximal end face 15b of the base part 15 is to be inserted. The insertion hole 45 extends in the axial direction of the body part 41, and is open at the end faces 41a and 41b. The inner surface of the body part 41 is composed of an end face side spaced part 46, an abutting face side spaced part 47, and a close contact part 48.

The end face side spaced part 46 defines an opening of the insertion hole 45 in the one end face (distal end face) 41a. The end face side spaced part 46 is radially outwardly spaced from the outer peripheral surface of the needle tube 5, and possesses a tapered shape such that the diameter of the insertion hole 45 increases toward the end face 41a. That is, as seen in FIG. 3, the inner diameter of the insertion hole 45 increases beginning at or near the close contact part 48 and extending distally. This helps ensure that the proximal end 5B side of the needle tube 5 protruding from the end face 15b of the base part 15 can be relatively easily inserted into the insertion hole 45. The shape of the end face side spaced part 46 of the insertion hole 45 is not limited to the tapered shape as described and shown, insofar as it is a shape that permits relatively easy insertion of the needle tube 5 into the insertion hole 45.

The abutting face side spaced part 47 defines an opening of the insertion hole 45 in the end face (abutting face) 41b. The abutting face side spaced part 47 is radially outwardly spaced from the outer peripheral surface of the needle tube 5, and possesses a tapered shape such that the diameter of the insertion hole 45 is continuously increased toward the end face 41b. With the elastic member 7 thus provided with the abutting face side spaced part 47, the body part 41 can be inhibited or prevented from being elastically deformed on the end face 41b side to cover the proximal end 5B of the needle tube 5.

The close contact part 48 is formed between the end face side spaced part 46 and the abutting face side spaced part 47. The close contact part 48 makes liquid-tight close contact with the outer peripheral surface of the needle 5. This helps prevent the medicine in the syringe 3 from penetrating between the needle tube 5 and the elastic member 7 to leak to the first member 11 side of the needle hub 6. In addition, the outer peripheral surface of the close contact part 48 makes liquid-tight close contact with the inner surface of the second member.

The flange part 42 is ring-shaped and projects radially outward from the outer peripheral surface of the body part 41. The outside diameter of the flange part 42 is approximately equal to the outside diameter of the base part 15 of the first member 11. A flat surface on one axially facing side of the flange part 42 abuts the engaging surface 37a of the engagement part 37 of the second member 12, while a flat surface on the other axially facing side abuts on the end face 15b of the base part 15 of the first member 11. The elastic member 7 is attached to the needle hub 6 by having its flange part 42 clamped between the engagement part 37 of the second member 12 and the base part 15 of the first member 11.

The stopper projection 43, like the flange part 42, is ring-shaped and projects radially outwardly from the outer peripheral surface of the body part 41. The stopper projection 43 engages the engaging surface 37b of the engagement part 37 of the second member 12. The flange part 42 and the stopper projection 43 of the elastic member 7 are engaged with the engagement part 37 of the second member 11, whereby the elastic member 7 is locked, or inhibited from moving in the axial direction. This can help prevent the medicine from penetrating between the elastic member 7 and the second member 12 to leak to the first member 11 side, thus enhancing the pressure resistance performance.

Examples of the material of the elastic member 7 include elastic materials such as various rubber materials such as natural rubber, silicone rubber, isobutylene rubber, etc., various thermoplastic elastomers based on polyurethane, styrene, or the like, and mixtures thereof.

[Syringe]

The syringe 3 includes a syringe body 51, and the discharge part 52 continuous with the syringe body 51. The syringe body 51 is composed of a cylinder (tube) having a circular cross-sectional shape. The discharge part 52 projects from one end in the axial direction of the syringe body 51, and is composed of a cylinder (tube) being circular in cross-section and smaller in outside diameter than the syringe body 51. The discharge part 52 possesses a tapered shape such that the outer diameter is continuously decreased along the distal direction. An end face 52a constituting the distal end of the discharge part 52 is a flat surface orthogonal to the axial direction, and abuts the end face (abutting face) 41b of the elastic member 7.

The outer peripheral surface of the discharge part 52 is provided with the screw part 53 for screw engagement with the second member 12 of the needle hub 6, and the syringe-side indication part 54. The syringe-side indication part 54 is recognized through the second member 12 of the needle hub 6 when the discharge part 52 is fitted into the fitting part 32 of the needle hub 6. When fitting the discharge part 52 into the fitting part 32 of the needle hub 6, the syringe-side indication part 54 coincides with the hub-side indication part 36 of the needle hub 6 in the circumferential direction as described above.

The medicine injection apparatus disclosed here may be so configured that the completion of the fitting of the discharge part 52 is recognized through coincidence of the hub-side indication part 36 and the syringe-side indication part 54 in the axial direction of the second member 12. For example, a structure may be adopted in which the hub-side indication part 36 is provided at the distal end of the fitting part 32 whereas the syringe-side indication part 54 is provided at an end portion on the discharge part 52 side of the syringe body 51. In that case, the coincidence of the hub-side indication part 36 and the syringe-side indication part 54 in the axial direction of the second member 12 can be recognized even if the second member 12 is not made to be transparent or semi-transparent.

A gasket is accommodated in the syringe body 51. An internal space of the syringe body 51 is partitioned in a liquid-tight manner by the gasket, and a space on one side which communicates with the discharge part 52 forms a liquid chamber 56 together with the internal space of the discharge part 52. In the other space in the syringe body 51, a plunger is disposed. The plunger is connected to the gasket, and protruded from an opening at the other end of the syringe body 51. With the plunger operated, the gasket is moved in the axial direction within the syringe body 51, whereby suction of a medicine into the liquid chamber 56 and discharge of the medicine filling the liquid chamber 56 are effected.

Examples of material(s) for the syringe body 51 and the discharge part 52 include synthetic resins such as polycarbonate, polypropylene, polyethylene, etc. Besides, glasses and the like may also be used as the material(s).

[Assembling Method for Injection Needle Assembly]

Figure 5A:
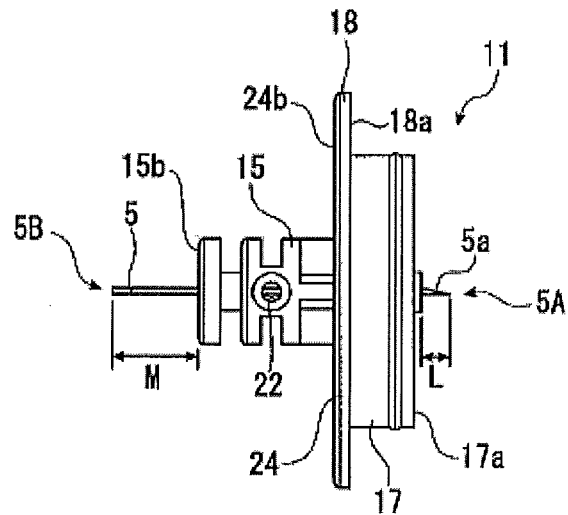
FIG. 5A is a side view showing the condition where a needle tube is held by a first member in the first embodiment of the medicine injection apparatus.
Figure 5B:
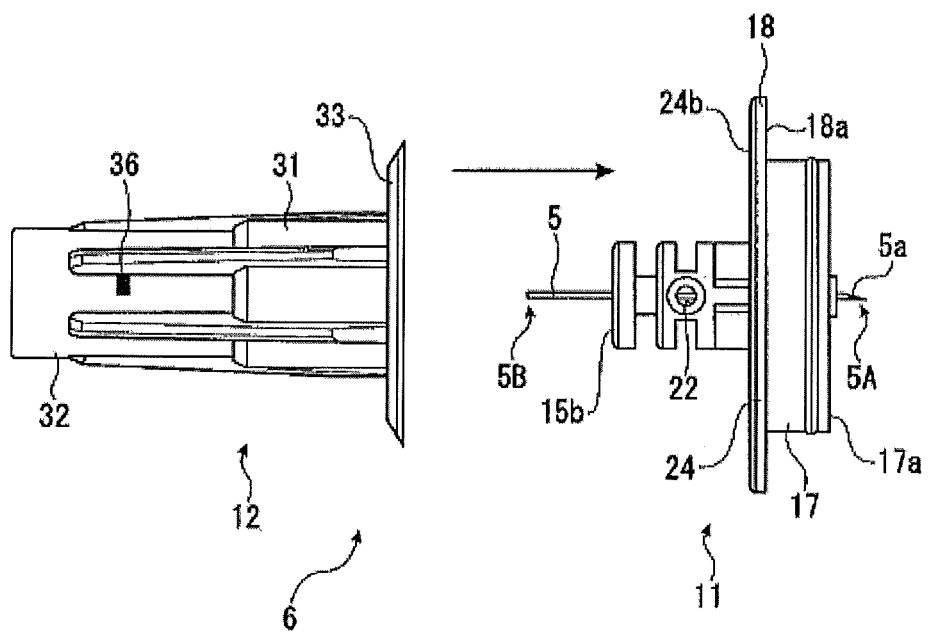
FIG. 5B is a side view illustrating the condition where a second member is connected to the first member holding the needle tube.

A method for assembling the injection needle assembly 2 will now be described below with reference to FIGS. 5A and 5B. FIG. 5A is a side view illustrating the needle tube 5 held by the first member 11, while FIG. 5B illustrates the second member 12 being connected to the first member 11 holding the needle tube 5.

To assemble the injection needle assembly 2, first the needle 5 is mounted to the first member 11. The length (protrusion length L) of that portion on the needle point 5A side of the needle tube 5 which protrudes distally from the needle protrusion surface 16a of the first member 11 is in the range of 0.9 to 1.4 mm. If the needle point 5A side of the needle tube 5 (i.e., the distal end of the needle 5) is held at the time of mounting the needle tube 5 to the first member 11, it may be difficult to stably hold the needle tube 5. As a result, the work of mounting the needle tube 5 would be troublesome.

On the other hand, the proximal end 5B side of the needle tube 5 is thereafter covered by the second member 12, so that the needle tube portion on this side can be set to an arbitrary length greater than the protrusion length L. In this embodiment, the length M of that portion on the proximal end 5B side of the needle tube 5 which protrudes from the end face 15b is greater than the protrusion length L. Therefore, at the time of mounting the needle tube 5 to the first member 11, that portion on the proximal end 5B side of the needle tube 5 which protrudes from the end face 15b of the base part 15 of the first member 11 is held. This makes it possible to stably hold the needle tube 5 and to relatively easily mount the needle 5 to the first member 11.

To mount the needle tube 5 to the first member 11, the needle 5 is passed through the through-hole 21 (see FIG. 3) in the first member 11, and the protrusion length L is adjusted as desired. Thereafter, the adhesive 20 (see FIG. 3) is injected through the injection hole 22 into the through-hole 21, to firmly attach the needle tube 5 to the base part 15 of the first member 11. By this, the work of mounting the needle tube 5 is completed, resulting in that the needle tube 5 is held by the first member 11.

The needle tube 5 can also be mounted to the first member 11 by insert molding. In that case, the needle point 5A side and the proximal end 5B side of the needle tube 5 are held by molds. This helps ensure that the posture of the needle tube 5 is stabilized, and yield can be enhanced.

Next, the second member 12 with the elastic member 7 engaged therein is connected to the first member 11 holding the needle tube 5. Specifically, the base part 15 of the first member 11 and the proximal end 5B side of the needle tube 5 are inserted into the insertion part 31 of the second member 12, and the connection piece 24 of the first member 11 is abutted on the fixation piece 34 of the second member 12. In this instance, the proximal end 5B side of the needle tube 5 is inserted in the insertion hole 45 of the elastic member 7 disposed inside the second member 12, and is put in liquid-tight close contact with the close contact part 48 (see FIG. 3). Thereafter, the fixation piece 34 of the second member 12 is firmly fixed to the connection piece 24 of the first member 11 by a fixing method such as adhesion with an adhesive, ultrasonic fusing, laser fusing, fixation with a set screw(s), or the like.

Consequently, the injection needle assembly 2 is assembled. Upon completion of the assembly of the injection needle assembly 2, the proximal end 5B side of the needle tube 5 is disposed inside the second member 12 in the state of being inserted in the elastic member 7. Therefore, at the time of mounting the needle hub 6 to the syringe 3 (see FIG. 2), contact of a finger or the like with the proximal end 5B side of the needle tube 5 can be avoided or obviated.

In the case of manufacturing an injection needle assembly in which the proximal end side of a needle does not protrude from a needle hub, in general the distal end side of the needle tube is held by hand. In the case where the protrusion length of the distal end side of the needle tube from the needle hub is set as short as about 0.5 to 3.0 mm, however, the needle tube cannot be stably held by hand, so that the required work is very troublesome and efficiency is lowered.

In the injection needle assembly 2 and the medicine injection apparatus 1 in this embodiment, the second member 12 is connected to the first member 11 holding the needle tube 5. In addition, the first member 11 holds the needle tube 5 in such a manner that both ends (the needle point 5A side and the proximal end 5B side) of the needle tube 5 protrude from the first member 11. Therefore, even when the protrusion length of the needle point 5A side of the needle tube 5 from the needle hub 6 is relatively small, the posture of the needle tube 5 can be stabilized by holding the proximal end 5B side of the needle 5, so that the operation of mounting the needle 5 to the needle hub 6 can be carried out relatively easily.

[Assembling Method for Medicine Injection Apparatus]

Now, a method for assembling the medicine injection apparatus 1 will be described below.

As shown in FIGS. 1 and 3, the medicine injection apparatus 1 is assembled by mounting the injection needle assembly 2 to the syringe 3. To mount the injection needle assembly 2 to the syringe 3, first, the discharge part 52 of the syringe 3 is inserted into the fitting part 32 of the injection needle assembly 2. Then, the screw part 53 provided on the discharge part 52 is screwed into the screw groove 35 of the fitting part 32, and the syringe-side indication part 54 of the discharge part 52 is made to coincide with the hub-side indication part 36 of the injection needle assembly 2 in the circumferential direction. By this, mounting of the injection needle assembly 2 to the syringe 3 is completed.

Upon completion of the assembly of the medicine injection apparatus 1, the end face 52a constituting the distal end of the discharge part 52 is perpendicularly brought into abutment on the end face (abutting face) 41b of the elastic member 7 in the injection needle assembly 2, and presses the end face 41b of the elastic member 7. This helps ensure that the end face 52a of the discharge part 52 and the end face 41b of the elastic member 7 are put in liquid-tight close contact with each other, and the needle hole of the needle tube 5 and the liquid chamber 56 of the syringe 3 communicate with each other. As a result, formation of a space between the distal end of the discharge part 52 and the proximal end 5B of the needle tube 5 is inhibited or prevented, and the residual amount of the medicine upon injection can be reduced. Moreover, the medicine filling the liquid chamber 56 of the syringe 3 can be prevented from leaking into the needle hub 6 of the injection needle assembly 2, and a predetermined amount of the medicine can be discharged via the needle point 5A of the needle tube 5.

Because the end face 52a of the discharge part 52 is perpendicularly brought into abutment on the end face 41b of the elastic member 7 so that both of them make liquid-tight close contact with each other, there is no need for precise adjustment of the position of the needle tube 5 relative to the needle hub 6 of the injection needle assembly 2. Therefore, the assembly of the needle hub 6 and the needle tube 5 can be simplified, and production efficiency can be enhanced.

Further, since the space between the proximal end 5B side of the needle tube 5 and the needle hub 6 is sealed by the elastic member 7, it is substantially ensured that at the time of suction (priming) of a medicine from a vial or the like, it is possible to inhibit or prevent a space from being formed between the outer peripheral surface of the proximal end 5B side of the needle tube 5 and the needle hub 6. In the case where a space is formed between the outer peripheral surface of the proximal end 5B side of the needle tube 5 and the needle hub 6, there arises a problem that at the time when the medicine filling the liquid chamber 56 is discharged via the needle point 5A of the needle tube 5, the air present in the space is compressed by the pressure for discharging the medicine, resulting in a buffering of pressure, whereby medicine stagnates in the space. Accordingly, where formation of a space between the outer peripheral surface of the proximal end 5B side of the needle tube 5 and the needle hub 6 is avoided or obviated, the amount of the medicine injected can be stabilized.

In addition, according to the injection needle assembly 2 and the medicine injection apparatus 1 in this embodiment, the elastic member 7 is provided with the abutting face side spaced part 47. Therefore, there is little or no possibility that the end face 41b of the elastic member 7 pressed by the end face 52a of the discharge part 52 might be elastically deformed so as to enter into the discharge part 52. Accordingly, the elastic member 7 can be inhibited or prevented from plugging up the needle hole on the proximal end 5B side of the needle tube 5.

[Method of Using Medicine Injection Apparatus]

Set forth below is a description of a method of using the disclosed medicine injection apparatus 1.

To puncture a living body with the needle point 5A of the needle tube 5, the end face 17a of the stabilization part 17 is first positioned to oppose the skin to be punctured. This results in the needle point 5A of the needle tube 5 being opposed to the skin to be punctured. Next, the medicine injection apparatus 1 is moved substantially perpendicularly to the skin to puncture the skin with the needle point 5A and, simultaneously, press the end face 17a of the stabilization part 17 against the skin. In this instance, the needle protrusion surface 16a contacts the skin, whereby the skin is deformed to be flat, and the needle point 5A side of the needle tube 5 punctures the skin by the protrusion length L.

Next, the end face 17a of the stabilization part 17 is pressed against the skin until the contact surface 18a of the guide part 18 comes into contact with the skin. Here, the guide part height Y (see FIG. 3) is set to such a value that the skin is punctured while the needle tube 5 and the stabilization part 17 are being pressed against the skin with proper pressures. Therefore, the pressure with which the stabilization part 17 presses the skin is set to a predetermined value.

As a result, the user can recognize the proper pressure relevant to the stabilization part 17, and can locate the needle point 5A and the bevel (blade surface) 5a of the needle tube 5 securely in the skin upper layer region. With the guide part 18 thus serving as a mark for permitting recognition of the proper pressure relevant to the stabilization part 17, the user can use the medicine injection apparatus 1 without anxiety.

In addition, with the stabilization part 17 abutting the skin, the posture of the medicine injection apparatus 1 is stabilized, and the needle 5 can puncture the skin in a straight manner. And it is possible to prevent the needle 5 from being moved after puncture, so that the medicine can be injected stably. In the case of a needle tube having an extremely small protrusion length of, for example, about 0.5 mm, the needle point may fail to pierce skin even when brought into abutment against the skin. Where the skin pressed by the stabilization part 17 is pressed down perpendicularly, however, the skin on the inner side of the stabilization part 17 is pulled, resulting in tension being applied to the skin. Therefore, the skin becomes less liable to escape from the needle point 5A of the needle 5. Accordingly, the stabilization part 17 can also facilitate puncture of the skin with the needle point 5A.

After the needle point 5A side of the needle 5 punctures the skin, the plunger of the syringe is pushed to move the gasket toward the discharge part 52 side. As a result, the medicine filling the liquid chamber 56 of the syringe 3 is pushed out from the discharge part 52, passes through the needle hole of the needle tube 5, and is injected via the needle point 5A into the skin upper layer region. In this instance, since no space is formed between the distal end of the discharge part 52 and the proximal end 5B of the needle tube 5, the residual amount of the medicine upon injection can be reduced.

Figure 6:
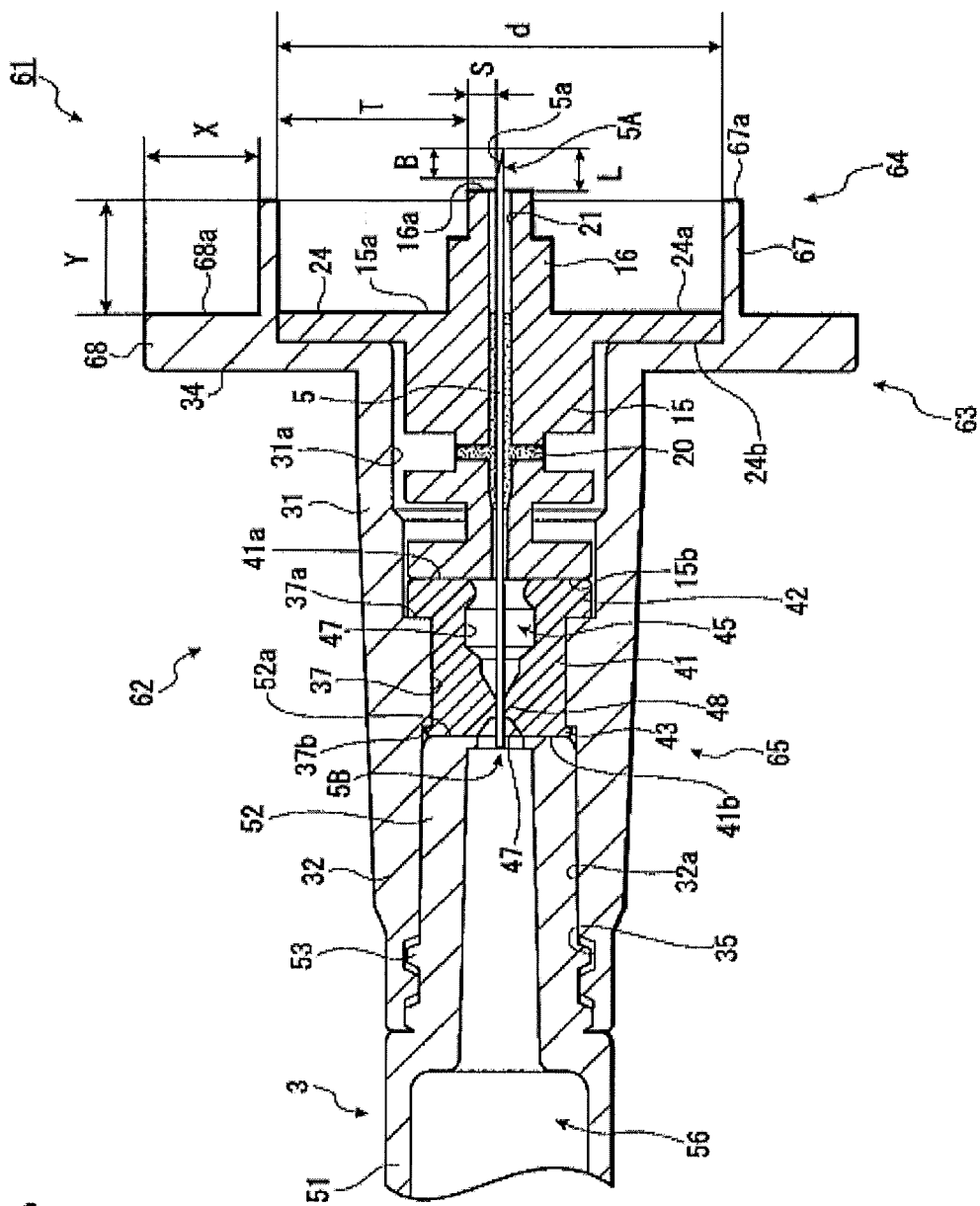
FIG. 6 is a cross-sectional view of a second embodiment of the medicine injection apparatus disclosed here.

A second embodiment of the medicine injection apparatus is illustrated in FIG. 6 and described below. As shown in FIG. 6, the medicine injection apparatus 61 includes an injection needle assembly 62, and a syringe 3 which is connected in a disconnectable manner from the injection needle assembly 62. The injection needle assembly 62 is configured similarly to the first embodiment of the injection needle assembly 2 described above and illustrated in FIGS. 1-5. The injection needle assembly 62 in this second embodiment differs from the first embodiment of the injection needle assembly 2 in that a second member 65 of a needle hub 63 is provided with a stabilization part 67 and a guide part 68. For this reason, the description here focuses primarily on the stabilization part 67 and the guide part 68. Other features of the injection needle assembly that are the same as in the injection needle assembly 2 described above are denoted by the same reference numerals and a detailed description of such features is not repeated.

The needle hub 63 includes a first member 64 which holds the needle tube (needle) 5, and a second member 65 in which the discharge part 52 of the syringe 3 is to be fitted. The first member 64 differs from the first member 11 in the first embodiment in that the connection piece 24 of the base part 15 is not provided with the stabilization part 17. Other features of the first member 64 are the same as those of the first member 11 and, hence, descriptions of those features is not repeated.

At the tip (radially outermost part) of the fixation part 34 provided on the second member 65, the stabilization part 67 and the guide part 68 are provided continuously. The stabilization part 67 is a cylindrical (tubular) shape which projects in the axial direction of the second member 65 and which covers or surrounds the periphery of an adjustment part 16 to be penetrated by the needle 5. Thus, the stabilization part 67 is radially outwardly spaced from the needle point 5A of the needle tube 5. A cap 8 (see FIG. 1) is detachably fitted to the stabilization part 67.

The end face 67a of the stabilization part 67 is located on the proximal side of the needle protrusion surface 16a of the adjustment part 16. However, the end face 67a may also be located on the same plane as the needle protrusion surface 16a or on the distal side of the needle protrusion surface 16a. The inside diameter d of the stabilization part 67 and the distance T from the inner wall surface of the stabilization part 67 to the peripheral edge of the needle protrusion surface 16a are the same as in the first embodiment described above.

The guide part 68 projects radially outward with reference to the second member 65, and has a contact surface 68a for contacting the skin. The contact surface 68a is a flat surface substantially parallel to the end face 67a of the stabilization part 67. The distance (hereinafter referred to as "guide part height") Y from the contact surface 68a of the guide part 68 to the end face 67a of the stabilization part 67 and the length (hereinafter referred to as "guide part length") X from the tip surface (radially outside surface) of the guide part 68 to the outer peripheral surface of the stabilization part 67 are the same as in the first embodiment.

In the injection needle assembly 62 and the medicine injection apparatus 61 thus configured, the residual amount of the medicine upon injection can be reduced, without needing a precise adjustment of the position of the needle tube 5 relative to the needle hub 63. In addition, the pressure with which the skin is pressed by the stabilization part 67 can be controlled to a predetermined value, and the guide part 68 serves as a mark for permitting recognition of a proper pressure relative to the stabilization part 67. Accordingly, the user can use the medicine injection apparatus 61 without anxiety.

Figure 7:
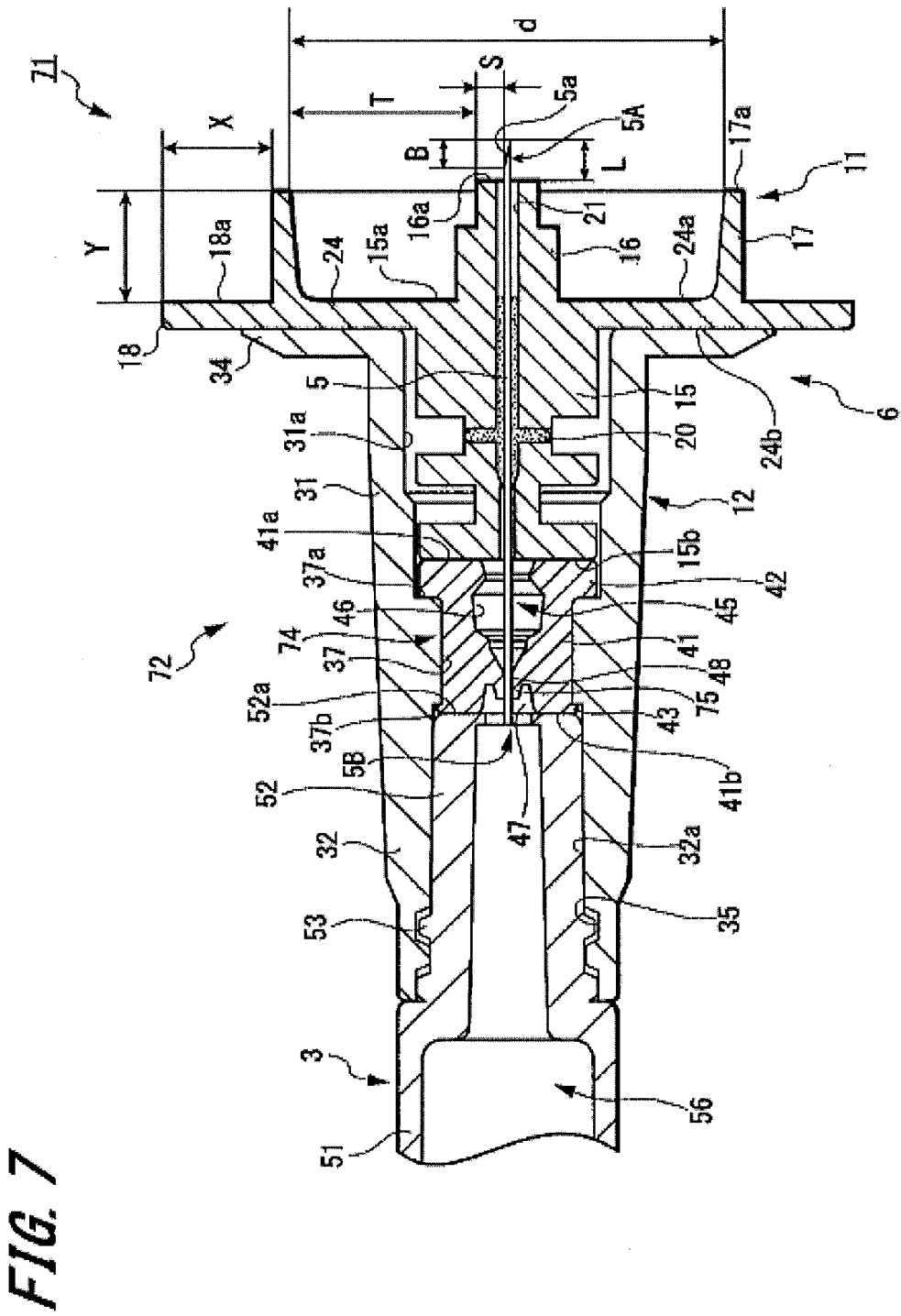
FIG. 7 is a cross-sectional view of a third embodiment of the medicine injection apparatus disclosed here.
Figure 8:
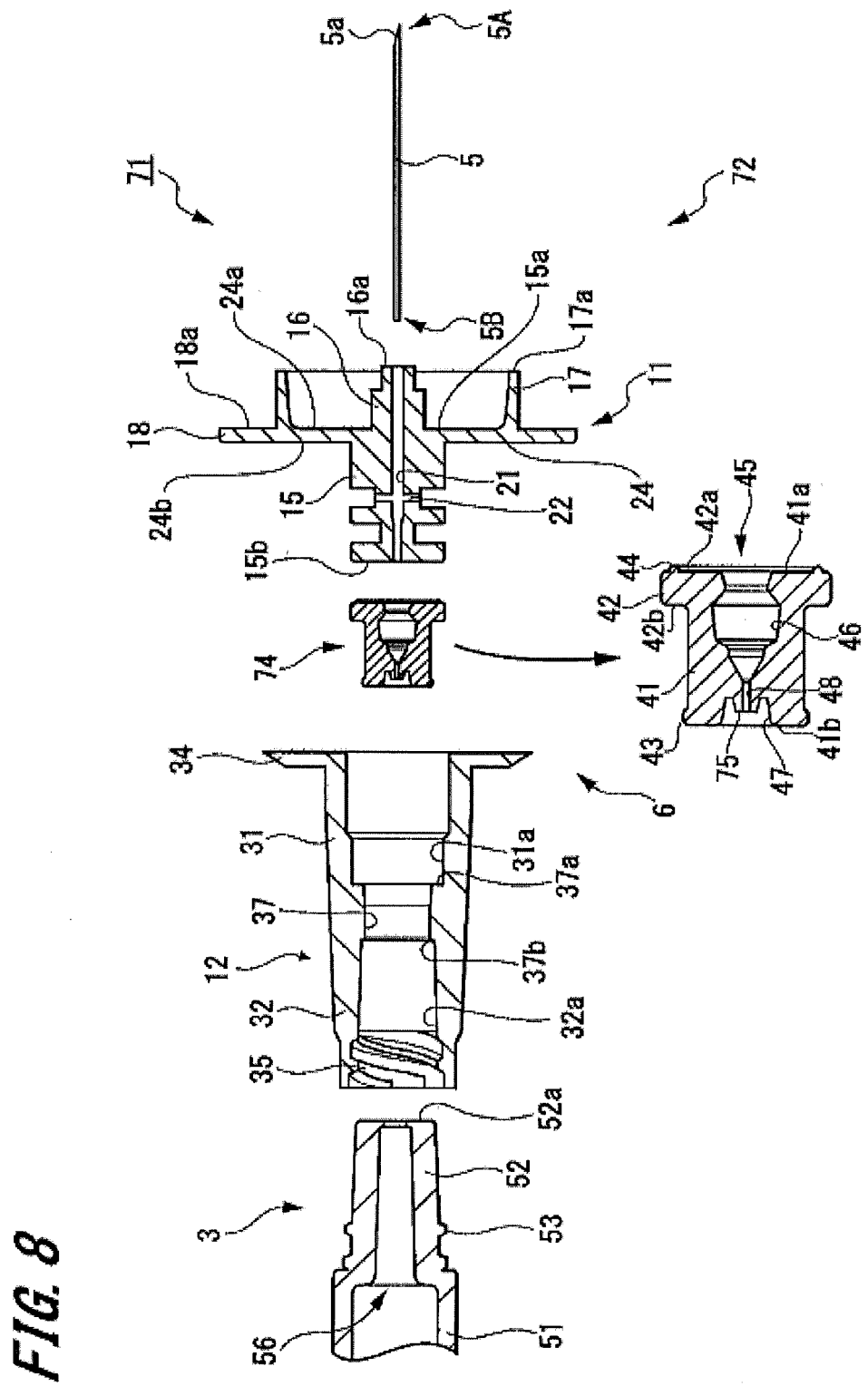
FIG. 8 is a cross-sectional view showing, in an exploded form, the third embodiment of the medicine injection apparatus.

A third embodiment of the medicine injection apparatus is illustrated in FIGS. 7 and 8. As shown in FIGS. 7 and 8, the medicine injection apparatus 71 includes an injection needle assembly 72, and a syringe 3 which is disconnectably connected to the injection needle assembly 72. The injection needle assembly 72 is configured similarly to the injection needle assembly 2 according to the first embodiment. This third embodiment of the injection needle assembly 72 differs from the first embodiment of the injection needle assembly 2 only in terms of the elastic member 74. Therefore, the discussion here focuses primarily on the elastic member 74. Other features of the injection needle assembly 72 that are the same as those in the injection needle assembly 2 discussed above and shown in FIGS. 1-5 are denoted by the same reference numerals, and a detailed description of such features is not repeated.

The injection needle assembly 72 in the medicine injection apparatus 71 includes the hollow needle tube (needle) 5 having a needle hole or longitudinally extending through hole, the needle hub 6 to which the needle 5 is fixed, the elastic member 74 disposed inside the needle hub 6, and the cap similar to the cap 8 shown in FIG. 1 which is detachably attached to the needle hub 6.

The elastic member 74 is disposed inside the second member 12 of the needle hub 6, and is interposed between the first member 11 and the syringe 3. The elastic member 74 includes a body part 41, a flange part 42 at one end in the axial direction of the body part 41, and a stopper projection 43 at the other end of the body part 41.

The body part 41 is cylindrically-shaped (inclusive of substantially cylindrically-shaped), and has end faces 41a and 41b which are orthogonal to the axial direction of the cylindrically-shaped body part. The end face 15b of the base part 15 of the first member 11 abuts one end face 41a of the body part 41, and the distal end of the discharge part 52 of the syringe 3 abuts the other end face 41b. In other words, the end face 41b constitutes an abutting face for abutting the distal end of the discharge part 52.

The body part 41 is provided with an insertion hole 45 in and through which the proximal end 5B side of the needle tube 5 protruding from the end face 15b of a base part 15 is inserted. The insertion hole 45 extends in the axial direction of the body part 41, and opens at both end faces 41a and 41b of the body part 41. The inner surface of the body part 41 is composed of an end face side spaced part 46, an abutting face side spaced part 47, and a close contact part 48.

The abutting face side spaced part 47 is provided with a needle-side valve element part 75. The needle-side valve element part 75 is a tubular projecting part covering the outer periphery of the needle 5. The outer peripheral surface of the needle-side valve element part 75 possesses a tapered shape such that the diameter continuously decreases toward the tip of the needle-side valve element part 75. When liquid medicine flows in the abutting face side spaced part 47, the needle-side valve element part 75 is pressed by the liquid medicine and is deformed to make close contact with the needle 5, whereby pressure resistance performance is enhanced.

The flange part 42 is formed in a ring-like shape projecting radially outward from an outer peripheral surface of the body part 41. The outside diameter of the flange part 42 is approximately equal to the outside diameter of the base part 15 of the first member 11. A flat surface 42a on one side of the flange part 42 is a flat surface which is the same as the end face 41a of the body part 41 described above. The flat surface 42a is provided with a ring-shaped (annular) projection 44. The ring-shaped projection 44 abuts on the end face 15b of the base part 15 of the first member 11 so it is collapsed. A flat surface 42b on the other side of the flange part 42 abuts on the engaging surface 37a of the engagement part 37 provided as part of the second member 12. The elastic member 74 is attached to the needle hub 6 by virtue of the flange part 42 of the elastic member 74 being clamped between the engagement part 37 of the second member 12 and the base part 15 of the first member 11.

The stopper projection 43, like the flange part 42, is ring-shaped and projects radially outward from the outer peripheral surface of the body part 41. The stopper projection 43 engages the engaging surface 37b of the engagement part 37 of the second member 12. The flange part 42 and the stopper projection 43 of the elastic member 74 engage the engagement part 37 of the second member 12, whereby the elastic member 74 is locked, or inhibited from moving in the axial direction. This helps prevent the liquid medicine from penetrating between the elastic member 74 and the second member 12 to leak to the first member 11 side. Thus, pressure resistance performance is enhanced.

Examples of the material for the elastic member 74 include elastic materials such as various rubber materials such as natural rubber, silicone rubber, isoprene rubber, etc., various thermoplastic elastomers based on polyurethane, styrene or the like, and mixtures thereof.

In the injection needle assembly 72 and the medicine injection apparatus 71 thus configured, also, the residual amount of the medicine upon injection can be reduced without need for precise adjustment of the position of the needle tube 5 relative to the needle hub 6. In addition, the pressure with which the skin is pressed by the stabilization part 17 can be controlled to a predetermined value, and the guide part 18 serves as a mark for permitting recognition of a proper pressure relevant to the stabilization part 17. Accordingly, the user can use the medicine injection apparatus 61 without anxiety.

Further, with the injection needle assembly 72 and the medicine injection apparatus 71 disclosed here, even in the case where the medicine discharged from the discharge part 52 of the syringe 3 has leaked to the abutting face side spaced part 47, the leaked medicine presses the needle-side valve element part 75, so that the needle-side valve element part 75 is pressed against the outer peripheral surface of the needle tube 5. By virtue of this, pressure resistance performance at a position between the needle tube 5 and the elastic member 74 can be enhanced. As a result, the medicine is less liable to leak to the side of the first member 11 of the needle hub 6, and the amount of the medicine injected into the skin upper layer region is stabilized.

A fourth embodiment of the injection needle assembly and the medicine injection apparatus disclosed here are described below with reference to FIG. 9.

The injection needle assembly and the medicine injection apparatus in the fourth embodiment are configured similarly to the injection needle assembly 72 and the medicine injection apparatus 71 in the third embodiment. The injection needle assembly and the medicine injection apparatus in this embodiment differ from the injection needle assembly 72 and the medicine injection apparatus 71 only in terms of the elastic member 81.

Figure 9:
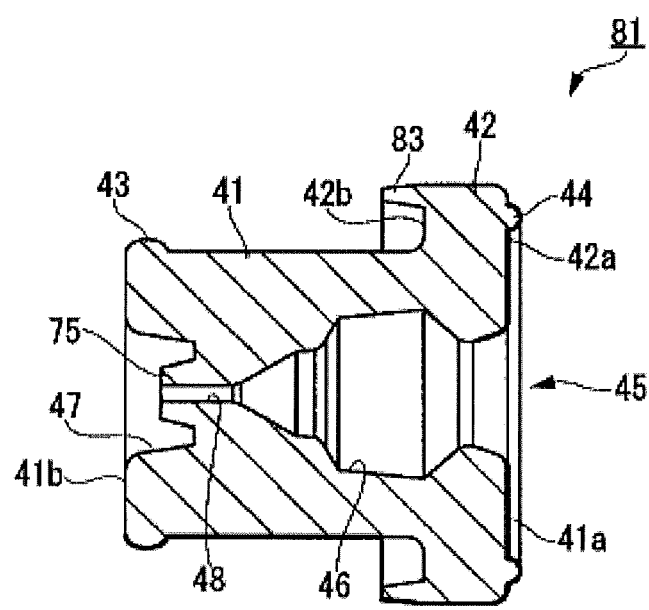
FIG. 9 is a cross-sectional view of an elastic member in a fourth embodiment of the medicine injection apparatus disclosed here.

As shown in FIG. 9, the elastic member 81 includes a second member side valve element part 83, in addition to a needle-side valve element body 75 of the elastic member 74 according to the third embodiment. The features of the elastic member 74 other than the second member side valve element part 83 are the same as in the elastic member 74 described above. The detailed description below thus focuses on the elastic member 81. Other features of the elastic member which are the same as described earlier are identified by common reference numerals, and a detailed description of such features is not repeated.

The second member side valve element part 83 is provided at the flat surface 42b on the other side of the flange part 42. The second member side valve element part 83 projects from the outer edge portion of the flat surface 42a, and extends continuously along the circumferential direction. When a liquid medicine discharged from the discharge part 52 of the syringe 3 has penetrated between the elastic member 81 and the inner surface of the second member 12, the second member side valve element part 83 is pressed by the medical liquid and urged into liquid-tight close contact with the inner surface of the second member 12. By virtue of this, the pressure resistance performance at a position between the elastic member 81 and the inner surface of the second member 12 is enhanced. The material of the elastic member 81 can be the same as that of the elastic member 74 in the first embodiment.

According to the fourth embodiment of the injection needle assembly and the medicine injection apparatus, the liquid medicine having leaked to the abutting face side spaced part 47 presses the needle-side valve element part 75, whereby the needle-side valve element part 75 is pressed against the outer peripheral surface of the needle tube 5 and deformed so as to make close contact with the needle tube 5. As a result, the pressure resistance performance at a position between the needle tube 5 and the elastic member 81 is enhanced. In addition, the liquid medicine having leaked into the gap between the body part 41 and the second member 12 presses the second member side valve element part 83 against the inner surface of the second member 12. Consequently, the second member side valve element part 83 is deformed so as to make close contact with the inner surface of the second member 12, whereby the pressure resistance performance at a position between the second member 12 and the elastic member 81 can be enhanced. As a result, the liquid medicine becomes less liable to leak to the side of the first member 11 of the needle hub 6, and the amount of the medicine injected into the skin upper layer region can be stabilized.

In the fourth embodiment described above, the flange part 42 of the elastic member 81 is provided with the second member side valve element part 83. However, the valve element to be pressed against the inner surface of the second member 12 may be so formed as to project from the outer peripheral surface of the body part 41 of the elastic member 81.

5. Experimental Example of Pressure Resistance Performance

Now, an experimental example carried out to verify the pressure resistance performance provided by the elastic member in the injection needle assembly and the medicine injection apparatus disclosed here is described below.

The experiment was conducted for the elastic member 74 (see FIG. 8) according to the third embodiment, the elastic member 81 (see FIG. 9) according to the fourth embodiment, and the elastic member 7 (see FIG. 4) according to the first and second embodiments.

In the experiment, a 33 gauge straight needle was used as the needle 5, and the needle 5 was fixed to the first member 11 of the needle hub 6 by use of a photo-curing adhesive. In the condition in which the elastic member is interposed between the first member 11 and the second member 12, and the needle 5 penetrates the elastic member, the first member 11 and the second member 12 were joined to each other by ultrasonic fusing; in this manner, injection needle assemblies were assembled individually on the basis of the kind of elastic member. Subsequently, syringes 3 were mounted respectively to the injection needle assemblies, to assemble medicine injection apparatuses individually on the basis of the kind of elastic member.

Next, the liquid chamber 56 of the syringe 3 was filled with a liquid, and the distal end of the needle 5 was sealed off. Subsequently, by use of a static testing apparatus (autograph), the plunger was pushed at a rate of 50 mm/min and rupture (breakdown) of each elastic member was detected. The rupture (breakdown) of each elastic member was detected from a strength-stroke curve obtained by the static testing apparatus, and the breaking strength of each elastic member was measured from the detection results. Next, the pressure exerted on each elastic member (pressure resistance performance) was calculated from the breaking strength and the cross-sectional area in a plane orthogonal to the axial direction of the discharge part 52 of the syringe 3.

Taking assembly errors and dimensional errors of the medicine injection apparatus into account, the experiment was carried out ten times for each kind of elastic member. Then, the minimum value, the maximum value and the mean value of the pressure exerted on the elastic member were calculated. The experimental results are shown in Table 1 below.

TABLE 1

Experimental results of pressure resistance performance

|  | Min. (MPa) | Max. (MPa) | Mean (MPa) |
| --- | --- | --- | --- |
| Elastic member 74 | 3.0 | 5.0 | 3.5 |
| Elastic member 81 | 3.5 | 5.0 | 3.7 |
| Elastic member 7 | 0.7 | 1.0 | 0.9 |

As shown in Table 1, when the elastic member 74 provided with the needle-side valve element part 75 was used, a pressure resistance performance of about 3.0 to 5.0 MPa was obtained. When the elastic member 81 provided with both the needle-side valve element part 75 and the second member side valve element part 83 was used, a pressure resistance performance of about 3.5 to 5.0 MPa was obtained. On the other hand, when the elastic member 7 not provided with any of the valve element parts 63, 83 was used, a pressure resistance performance of about 0.7 to 1.0 MPa was obtained.

Thus, it was confirmed that the elastic member 74 provided with the needle-side valve element part 75 and the elastic member 81 provided with both the needle-side valve element part 75 and the second member side valve element part 83 are higher in pressure resistance (pressure resistance performance was enhanced), as compared with the elastic member 7 not provided with a valve element.

In addition, though not shown in Table 1, it was confirmed that the elastic member 74 provided with the needle-side valve element part 75 is higher in pressure resistance than an elastic member provided only with the second member side valve element part 83. From this, it was found that pressure resistance performance is enhanced more when a valve element to be pressed against the outer peripheral surface of the needle tube 5 is provided than when a valve element to be pressed against the inner surface of the second member 12 is provided.

Embodiments of the medicine injection apparatus and the injection needle assembly disclosed here have been described above, together with operations of the apparatus/assemblies. However, the injection needle assembly and the medicine injection apparatus are not limited solely to the above-described embodiments, and various modifications are possible without departing from the scope of the invention as defined by the claims.

For example, in the first to fourth embodiments described above, the end face 52a of the discharge part 52 of the syringe 3 is perpendicularly brought into abutment on the end face 41b of the elastic member 7 (74, 81). However, communication between the liquid chamber 56 of the syringe 3 and the needle tube 5 can be secured, even if the end face 52a of the discharge part 52 does not abut the end face 41b of the elastic member 7 (74, 81). Therefore, the end face of the discharge part may not necessarily abut on the end face of the elastic member. For instance, the end face 52a of the discharge part 52 may not abut on the end face 41b of the elastic member 7, in the case where scattering (dispersion) as to the dimensions of the syringe 3, the second member 12 or the elastic member 7 or scattering (dispersion) as to the method of assembling by the user is generated.

The apparatus/assemblies disclosed here allow for such scattering (dispersion), eliminate the need for precise positioning, and produce a high effect.

In order to reduce the dead volume, it is preferable to shorten or eliminate the distance between the end face 52a and the end face 41b.

In the first to fourth embodiments described above, the proximal end 5B of the needle tube 5 is inserted in the discharge part 52 of the syringe 3. However, the proximal end 5B of the needle tube 5 need not necessarily be inserted in the discharge part 52 of the syringe 3. For example, the proximal end 5B of the needle tube 5 may be located substantially on the same plane as the end face 52a of the discharge part 52.

In the embodiments described above, the discharge part 52 of the syringe 3 is brought into screw engagement with the fitting part 32 of the needle hub 6 (63). However, the discharge part 52 may be connected to the fitting part 32 by fitting alone. In that case, like in the first to fourth embodiments, it is recommendable that the discharge part 52 is formed in a tapered shape such that the diameter is continuously decreased along the distal direction. This helps ensure that even when the dimensions of the discharge part 52 and the fitting part 32 are scattered on a manufacture basis (i.e., dimensional tolerances exist), the end face 52a of the discharge part 52 and the end face 41b of the elastic member 7 (74, 81) can be put into liquid-tight close contact with each other.

In the first to fourth embodiments, the needle hub 6 (63) is provided with the stabilization part 17 (67) and the guide part 18 (68). However, the syringe may be provided with the stabilization part and the guide part as an alternative.

The detailed description above describes embodiments of the injection needle assembly and the medicine injection apparatus disclosed here. The invention is not limited, however, to the precise embodiment and variations described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An injection needle assembly comprising:
    a needle possessing a proximal end portion and a sharp distal end portion to puncture skin, the needle comprising a through hole extending along a longitudinal extent of the needle and opening to the sharp distal end portion and to the proximal end portion of the needle;
    a first member possessing a through hole extending between proximal and distal ends of the first member, the through hole of the first member being open at the proximal end of the first member and being open at the distal end of the first member;
    the needle being positioned in the through hole in the first member and being fixed in place in the through hole in the first member such that the sharp distal end of the needle projects distally beyond a distal end face of a distal end portion of the first member so the sharp distal end portion is exposed to puncture the skin and such that the proximal end of the needle projects proximally beyond a proximal end face of a proximal end portion of the first member so the proximal end of the needle is exposed;
    a second member possessing a through hole so the second member possesses an inner surface, the through hole of the second member extending between proximal and distal ends of the second member, the through hole in the second member being open at the proximal end of the second member and being open at the distal end of the second member, a proximal end portion of the through hole in the second member being configured to receive a discharge part of a syringe;
    the proximal end portion of the first member being positioned inside the second member so that an outer peripheral surface of the proximal end portion of the first member faces the inner surface of the second member; and
    an elastic member disposed inside the second member, the elastic member possessing an outer peripheral surface in liquid-tight contact with the inner surface of the second member, the elastic member also comprising an insertion hole extending throughout a longitudinal extent of the elastic member so that the elastic member possesses an inner surface, a portion of the inner surface of the elastic member being in liquid-tight contact with an outer peripheral surface of the needle;
    wherein the elastic member includes an abutting end face at an axial end of the elastic member that is adapted to abut against the discharge part of the syringe, the elastic member including a needle side valve element part adjacent the abutting end face of the elastic member, the portion of the inner surface of the elastic member that is in liquid-tight contact with the outer peripheral surface of the needle being the inner surface of the needle side valve element part, the needle side valve element part possessing an outer surface with a tapering outer diameter so that pressure applied to the tapering outer diameter by liquid medicine discharged from the discharged part of the syringe presses the inner surface of the needle side valve element part toward the outer peripheral surface of the needle.

2. The injection needle assembly according to claim 1, wherein the elastic member possesses a first abutting end face which abuts the proximal end face of the proximal end portion of the first member.

3. The injection needle assembly according to claim 2, wherein the elastic member has a second abutting end face at an axial end of the elastic member opposite the first abutting end face, the second abutting end face being adapted to abut against the discharge part of the syringe, the elastic member possessing an opening at the second abutting end face which communicates with the insertion hole, the opening at the second abutting end face having an inner surface radially outwardly spaced from the outer peripheral surface of the needle.

4. The injection needle assembly according to claim 1, wherein the elastic member includes an outwardly projecting flange part which is clamped between the first member and the second member.

5. The injection needle assembly according to claim 1, wherein the elastic member includes a second member side valve element part which is pressed against the inner surface of the second member when pressure is applied to the second member side valve element part by the liquid medicine discharged from the discharge part of the syringe.

6. An injection needle assembly comprising:
    a needle possessing a needle point to puncture skin of a living body;
    a needle hub including a first member which holds the needle, and a second member in which a discharge part of a syringe is to be fitted; and
    an elastic member disposed inside the second member in liquid-tight close contact with an inner surface of the second member, the elastic member having an insertion hole in which the needle is positioned;
    wherein the elastic member includes a first needle side valve element part possessing an outer surface configured so that pressure exerted on the outer surface of the first needle side valve element part by liquid medicine discharged from the discharge part of the syringe presses an inner surface of the first needle side valve element part against an outer peripheral surface of the needle.

7. The injection needle assembly according to claim 6, wherein the elastic member has an abutting face adapted to abuts a distal end of the discharge part of the syringe.

8. The injection needle assembly according to claim 7, wherein the elastic member includes an abutting face side spaced part which is at a side of the elastic member at which is located the abutting face, the abutting face side spaced part forming an opening of the insertion hole at the abutting face and which is radially outwardly spaced from an outer peripheral surface of the needle.

9. The injection needle assembly according to claim 6, wherein the elastic member has an end face disposed on a side opposite the abutting face, the elastic member including an end face side spaced part at the side of the elastic member at which is located the end face, the end face side spaced part forming an opening of the insertion hole at the end face of the elastic member and being spaced radially outwardly from the outer peripheral surface of the needle.

10. The injection needle assembly according to claim 6 wherein the elastic member has a radially outwardly extending flange part which is clamped between the first member and the second member.

11. The injection needle assembly according to claim 6, wherein the elastic member includes a second member side valve element part possessing an inner surface configured so that pressure exerted on the inner surface of the second member side valve element part by the liquid medicine discharged from the discharge part of the syringe presses an outer surface of the second member side valve element part against an inner surface of the second member.

12. The injection needle assembly according to claim 6, wherein the first member fixedly holds the needle so that both ends of the needle protrude from the first member, and the second member is connected to the first member and surrounds a proximal portion of the needle protruding from the first member.

13. The injection needle assembly according to claim 6, wherein a proximal portion of the needle proximally protrudes from the first member by a first length, and a distal portion of the needle distally protrudes from the first member by a second length, the first length being smaller than the second length.

14. The injection needle assembly according to claim 6, wherein an inner surface of the second member includes a screw groove for screw engagement with the syringe.

15. The injection needle assembly according to claim 6, wherein the second member includes a recognition part for permitting a user to recognize that fitting of the discharge part of the syringe into the second member is completed.

16. The injection needle assembly according to claim 6, further comprising an adjustment part possessing a needle protrusion surface peripherally encircling a distal portion of the needle and adapted to abut the skin when the needle point of the needle punctures the skin, the needle point projecting distally beyond the needle protrusion surface.

17. The injection needle assembly according to claim 16, wherein the adjustment part is integrally formed in one piece with the first member.

18. The injection needle assembly according to claim 6, wherein the needle hub includes a stabilization part radially outwardly spaced from the needle point of the needle and adapted to contact the skin when the needle point of the needle punctures the skin of the living body.

19. The injection needle assembly according to claim 18, wherein the stabilization part is integrally formed in one piece with the first member.

20. The injection needle assembly according to claim 6, wherein the needle is 26 to 33 gage.

* * * * *